United States Patent [19]

Umezawa et al.

[11] Patent Number: 4,833,268
[45] Date of Patent: May 23, 1989

[54] THREO-ADRENALINECARBOXYLIC ACID, AND THE PRODUCTION AND USES THEREOF

[75] Inventors: Hamao Umezawa, Tokyo; Toshiharu Nagatsu, Yokohama; Hirotaro Narabayashi, Tokyo; Tomio Takeuchi, Tokyo; Shuichi Iwadare, Tokyo; Ikuo Matsumoto, Machida; Junji Yoshizawa, Machida; Hajime Morishima, Tokyo; Koji Tomimoto, Kawasaki, all of Japan

[73] Assignee: Zaidan Hojin Biseibutsu Kagaku Kenkyu Kai, Tokyo, Japan

[21] Appl. No.: 80,165

[22] Filed: Jul. 30, 1987

Related U.S. Application Data

[63] Continuation of Ser. No. 768,345, Aug. 22, 1985, abandoned, which is a continuation-in-part of Ser. No. 523,957, Aug. 17, 1983, abandoned.

[30] Foreign Application Priority Data

Dec. 20, 1982 [JP] Japan ................. 57-221797

[51] Int. Cl.$^4$ ............................................. C07C 101/32
[52] U.S. Cl. ..................................... 562/444; 514/567
[58] Field of Search ............................................. 562/444

[56] References Cited

U.S. PATENT DOCUMENTS

| | | | |
|---|---|---|---|
| 2,868,818 | 1/1959 | Pfister et al. | 562/446 |
| 3,178,472 | 4/1965 | Hellenback et al. | 562/444 |
| 3,859,331 | 1/1975 | Kaiser et al. | 562/446 |
| 3,891,696 | 6/1975 | Bodor et al. | 562/446 |
| 3,920,728 | 11/1975 | Hegedus et al. | 562/446 |
| 4,319,040 | 3/1982 | Ohashi et al. | 562/444 |
| 4,391,786 | 7/1983 | Umeyawa | 562/444 |

*Primary Examiner*—James H. Reamer
*Attorney, Agent, or Firm*—Larson and Taylor

[57] ABSTRACT

DL- or L-Threo-3-(3,4-dihydroxyphenyl)-N-methylserine which may also be termed as DL- or L-threo-adrenalinecarboxylic acid are now provided, which are new compounds useful for therapeutic treatment of Parkinson's disease and mental depression disease. DL-Adrenalinecarboxylic acid may be produced by a new process comprising reacting glycine with O-protected 3,4-dihydroxybenzaldehyde, hydrolyzing the resultant reaction product under acidic conditions to form O-protected DL-3-(3,4-dihydroxyphenyl)serine, isolating the O-protected DL-3-(3,4-dihydroxyphenyl)serine into the threo isomer and the erythro isomer by recrystallization from a suitable organic solvent, introducing an unsubstituted or substituted benzyl group into the 2-amino group of the resulting O-protected DL-threo-3-(3,4-dihydroxyphenyl)serine, then N-methylating the resulting O-protected DL-threo-3-(3,4-dihydroxyphenyl)-N-benzylserine, and removing the O-protecting groups as well as the unsubstituted or substituted benzyl group at the 2-methylamino group of the N-methylation product.

L-Adrenalinecarboxylic acid may be produced by a new process comprising introducing a p-methoxybenzyloxycarbonyl group into the 2-amino group of the O-protected DL-threo-3-(3,4-dihydroxyphenyl)serine obtained as an intermediate product, optically resolving the resultant O-protected DL-threo-3-(3,4-dihydroxyphenyl)-N-p-methoxybenzyloxycarbonyl-serine by reacting the latter with an optically active amine and recrystallizing the resultant amine salt products from a suitable organic solvent, removing the p-methoxy-benzyloxycarbonyl group from the resultant O-protected L-threo-(3,4-dihydroxyphenyl)-N-p-methoxybenzyloxycarbonyl-serine, reacting the resultant O-protected L-threo-(3,4-dihydroxyphenyl)serine with dimethyl sulfate in dry acetone to form an O-protected L- or D-threo-(3,4-dihydroxyphenyl)-N-methylserine methyl ester, saponifying this methyl ester and then removing the O-protecting groups from the saponification product.

2 Claims, No Drawings

THREO-ADRENALINECARBOXYLIC ACID, AND THE PRODUCTION AND USES THEREOF

This application is a continuation of application Ser. No. 768,345 filed Aug. 22, 1985, now abandoned, which is a continuation-in-part of application Ser. No. 523,957 filed Aug. 17, 1983, now abandoned.

SUMMARY OF THE INVENTION

This invention relates to DL- or L-threo-3-(3,4-dihydroxyphenyl)-N-methylserine which is a new compound possessing therapeutically useful activities and particularly useful for the therapeutic treatment of Parkinson's disease and mental depression disease. This invention also relates to processes for the production of the new compound. This invention further relates to the therapeutic uses of the new compound.

BACKGROUND OF THE INVENTION

It is known that Parkinson's disease, namely parkinsonism is such disease which is caused by abnormal reduction or decrease in the levels of catecholamines such as dopamine, noradrenaline and adrenaline present in the brain of the human beings (see, for example, "Advances in Neurology" Vol. 24, pages 29–36 (1979) and Vol. 40, pages 467–473 (1984); and the "Biochemical Medicine" Vol. 27, pages 317–324 (1982)). It is expectable that the parkinsonism can be treated therapeutically by supplementing externally the biogenic catecholamines or their precursors into the parkinsonian patients so that the levels of the catecholamines as descreased can be increased and restored to the normal levels in the brain. L-3,4-dihydroxyphenylalanine (L-DOPA) and L-threo-3-(3,4-dihydroxyphenyl)serine (L-threo-DOPS) as synthetized are administered to parkinsonian patients as such a precursor of said catecholamine which would be capable of penetrating and transferring into the parkinsonian brain through the blood-brain barrier and increasing the abnormally decreased levels of the brain catecholamines to the normal levels, even when such precursor is administered intraperitoneally or intravenously.

It was fairly long ago that 3-(3,4-dihydroxyphenyl)serine (abbreviated as DOPS) was first synthetized, but only in recent years, physiological and pharmacological activities of this known compound (DOPS) have become noticeably interesting in the related field of the art. Thus, several years ago, it was reported that L-threo-DOPS is useful as an antiparkinsonian drug for use in therapeutic treatment of Parkinson's disease (see Japanese patent application prepublication "Kokai" No. 125630/77 and U.S. Pat. No. 4,319,040), and also as an antidepressive agent for use in therapeutic treatment of mental disease, depression (see Japanese patent application prepublication "Kokai" No. 20747/80 and U.S. Pat. No. 3,920,728), and further that L-erythro-DOPS is useful as a hypertensive agent for use in therapeutic treatment of hypertension. Judging from these useful biological activities of DOPS, we, the present inventors have an expection that new N-methylated derivatives of DOPS will show any biological activities similar to or higher than or more valuable than those of DOPS and thus be useful as medical substance in the therapeutic applications.

Furthermore, it is known that the four stereoisomers of DOPS includes L-erythro-DOPS, D-erythro-DOPS, L-threo-DOPS and D-threo-DOPS. Biochemical and histochemical investigations of these four stereoisomers of DOPS have revealed that L-erythro-DOPS and L-threo-DOPS as intraperitoneally administered in rats are readily decarboxylated in vivo, leading to an accumulation of noradrenaline (namely, norepinephrine) in heart, and that the accumulation of noradrenaline of the unnatural (d)-form in brain is significant after the intraperitoneal administration of L-erythro-DOPS, whereas the accumulation of noradrenaline of the natural (l)-form in brain is negligible after the intraperitoneal administration of L-threo-DOPS but the accumulation of the natural (l)-noradrenaline in the brain becomes marked after direct injection of L-threo-DOPS into a cerebral ventricle, indicating that L-threo-DOPS as given intraperitoneally can hardly penetrate and transfer through the blood-brain barrier into the brain and is considered to be substantially not effective to increase the level of noradrenaline in the brain (see "The Journal of Pharmacology and Experimental Therapeutics" Vol. 193. No. 2, pages 523–530 (1975)). It also has been revealed in said literat that intraperitoneal administration of high dosages of D-erythro-DOPS or D-threo-DOPS causes a slight increase in the levels of noradrenaline in heart and brain, indicating that D-erythro-DOPS and D-threo-DOPS are probably not decarboxylated in vivo to a major extent.

We have now succeeded in synthetizing firstly as the new compound threo-3-(3,4-dihydroxyphenyl)-N-methylserine, either in the DL-form or in the L-form (as viewed from the α-carbon atom of the serine moiety) with starting from DL-threo-DOPS, and we have now found that, in contrast to the known L-threo-DOPS, the new compound, L-threo-3-(3,4-dihydroxyphenyl)-N-methylserine, even when administered intraperitoneally or intravenously in mice, can surprisingly penetrate and transfer through the blood-brain barrier into the brain so that a quantity of L-threo-3-(3,4-dihydroxyphenyl)-N-methylserine is detectable in the brain of the treated mice, with an increased level of adrenaline in the brain which is significantly higher than the normal level of adrenaline in the brain of the mice untreated, and further we have now found that L-threo-3-(3,4-dihydroxyphenyl)-N-methylserine can hardly be decarboxylated into adrenaline in "in vitro" tests where L-threo-3-(3,4-dihydroxyphenyl)-N-methylserine is treated with such a homogenates of the whole brains of mice which is containing therein some catecholamine-related enzymes, including at least an enzyme for converting L-threo-DOPS into noradrenaline as well as an enzyme, phenylethanolamine N-methyltransferase (PNMT) for converting noradrenaline as substrate into adrenaline, in contrast to the experimental fact that L-threo-DOPS can be decarboxylated into noradrenaline in the "in vitro" tests where L-threo-DOPS is treated with the above-mentioned homogenate of the whole brains of mice.

We have not yet been able to elucidate why the level of adrenaline in brain can virtually be increased by intraperitoneal or intravenous injection of the new compound L-threo-3-(3,4-dihydroxyphenyl)-N-methylserine which can hardly be decarboxylated in the "in vitro" tests using the homogenate of the whole brains containing all the enzymes of the brain.

From these experimental facts as above, we have expected that the new compound, L-threo-3-(3,4-dihydroxyphenyl)-N-methylserine which may also be termed as L-threo-adrenalinecarboxylic acid, and a pharmaceutically acceptable salt and hydrate thereof will be more advantageous and more promising as medicinal agent than anyone of the known four stereoisomers of DOPS.

It is further known that the L-threo isomer of DOPS exhibits the antiparkinsonian activity while the L-erythro isomer thereof cannot exhibit such medicinal activity (see Japanese patent application prepublication "Kokai" No. 125630/77 as referred to herein before). Besides, T. Nagatsu, one of the inventors, has found the fact that not only noradrenaline, but also adrenaline in the brain are decreased in patients with Parkinson's disease. From this point of view, we presume that the L-threo form will be necessary for the antiparkinsonian activity of the 3-(3,4-dihydroxyphenyl)-N-methylserine we have now synthetized. And we have now confirmed that the DL-form and the L-threo isomer of 3-(3,4-dihydroxyphenyl)-N-methylserine synthetized by us are virtually highly effective for the medicinal applications.

For our acknowledgement, we may add that a previous approach to the synthesis of 3-(3,4-dihydroxyphenyl)-N-methylserine was reported by F. G. Mann and C. E. Dalgliesh in the "Journal of Chemical Society" page 658 (1947) and also in the "Nature" 158, 375 (1946). They reported that this 3-(3,4-dihydroxyphenyl)-N-methylserine was obtained in a poor yield of only 3.5% by starting from 3,4-diethoxycarbonyloxybenzaldehyde and sarcosine methyl ester, and by interacting these compounds with each other and hydrolyzing the resultant 3-(3,4-diethoxycarbonyloxyphenyl)-N-methylserine methyl ester, followed by the deprotection of the protected 3- and 4-hydroxyl groups. However, they did not refer at all to the stereo chemistry of the 3-(3,4-dihydroxyphenyl)-N-methylserine they synthetized. It is therefore not known that said compound so synthetized by F. G. Mann et al was actually either in the threo-form or in the erythro-form or in the form of a mixture of the threo- and erythro-forms.

In the course of our study about the synthesis of 3-(3,4-dihydroxyphenyl)-N-methylserine, we have found that a 3-(3,4-dihydroxyphenyl)serine derivative of the general formula (II):

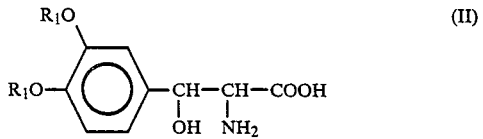

wherein $R_1$ represents a phenolic hydroxy-protecting group, preferably an aralkyl group such as benzyl, which is obtainable by interaction of 1 molar proportion of glycine with 2 molar proportions of an O-protected 3,4-dihydroxybenzaldehyde of the formula

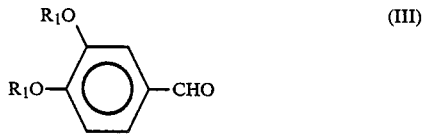

wherein $R_1$ is as defined above in a known manner, can be isolated into the separate threo- and erythro-isomers. Based on this discovery and by our success in the subsequent conversion of each of these separate isomers so isolated into the corresponding N-methyl derivative while maintaining its original configuration, we have now successfully synthetized DL-threo-3-(3,4-dihydroxyphenyl)-N-methylserine and DL-erythro-3-(3,4-dihydroxyphenyl)-N-methylserine, respectively.

DL-Threo-3-(3,4-dihydroxyphenyl)-N-methylserine thus synthetized by us has never been described in any literature, but is believed to be a new compound. It is note worthy that the melting point of the DL-threo-3-(3,4-dihydroxyphenyl)-N-methylserine so produced by us is 163°–165° C. (with decomposition) which is clearly different from the melting point (221°223° C. with decomposition) of the DL-erythro-3-(3,4-dihydroxyphenyl)-N-methylserine so produced by us and also is far different from the melting point (233° C. with decomposition) given by C. E. Dalgliesh et al in the literature for their 3-(3,4-dihydroxyphenyl)-N-methylserine.

Furthermore, we have now succeeded in isolating L-threo-3-(3,4-dihydroxyphenyl)-N-methylserine from the DL-form of threo-3-(3,4-dihycroyphenyl)-N-methylserine according to a particular optical resolution method we have now devised and described hereinafter.

DETAILED DESCRIPTION OF THE INVENTION

According to a first aspect of this invention, therefore, there is provided as the new compound, L-threo-3-(3,4-dihydroxyphenyl)-N-methylserine represented by the formula (I):

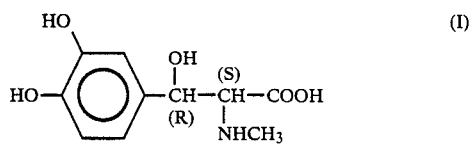

wherein (S)* denotes (S)-configuration and (R) denotes (R)-configuration, or pharmaceutically acceptable salt or hydrate thereof.

During our investigation on the synthesis of the threo-3-(3,4-dihydroxyphenyl)-N-methylserine, we have further found that the N-methylation of threo-DOPS, if applied directly to the amino group of an O-protected threo-DOPS, is unsuccessful because of its permethylation involved and that the desired mono-N-methylation of the threo-DOPS can be achieved smoothly and successfully when applied thereto after the amino group of the starting O-protected threo-DOPS have been blocked with an unsubstituted or substituted benzyl group of the formula

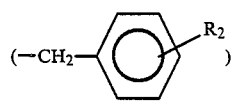

where $R_2$ represents a hydrogen atom, a lower ($C_1$–$C_6$) alkyl or lower ($C_1$–$C_6$) alkoxy group, and further that the subsequent removal of both the O-protecting groups ($R_1$) and the blocking benzyl group

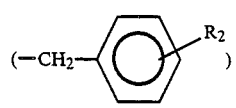

from the N-methylation product can be attained in a conventional manner known per se, without affecting the configuration of the N-methylation product, thus affording the desired DL-threo-3-(3,4-dihydroxyphenyl)-N-methylserine in a favorably high yield.

According to a second aspect of this invention, therefore, there is provided a process for the production of DL-threo-3-(3,4-dihydroxyphenyl)-N-methylserine, which comprises the steps of:

(a) introducing an unsubstituted or substituted benzyl group of the formula

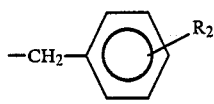
(IV)

wherein $R_2$ represents a hydrogen atom, a lower alkyl group or a lower alkoxyl group, into the amino group at the 2-position of an O-protected DL-threo-3-(3,4-dihydroxyphenyl) serine of the formula (II'):

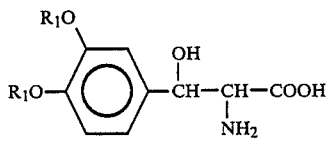
(II')

wherein $R_1$ represents a group for protecting the phenolic hydroxyl group, preferably an aralkyl group such as benzyl (b) N-methylating the resultant O-protected DL-threo-3-(3,4-dihydroxyphenyl)-N-benzylserine of the formula (V):

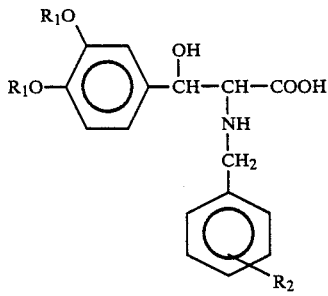
(V)

wherein $R_1$ and $R_2$ are as defined above, to form the N-methyl derivative of the O-protected DL-threo-3-(3,4-dihydroxyphenyl)-N-benzylserine represented by the formula (VI):

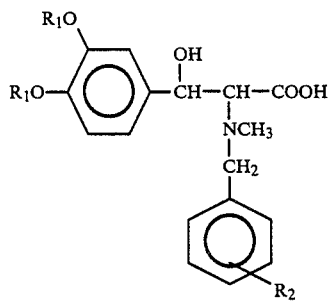
(VI)

wherein $R_1$ and $R_2$ are as defined above, and (c) removing the N-blocking benzyl group of the formula

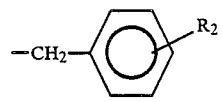

and the O-protecting groups ($R_1$) from said N-methyl drivative to produce the desired DL-threo-3-(3,4-dihydroxyphenyl)-N-methylserine.

The reaction for introduction of the benzyl group of the formula (IV) as well as the reactions for removal of the N-blocking benzyl group of the formula (IV) and for removal of the O-protecting groups $R_1$ may readily be effected by conventional methods known in the protection and deprotection techniques for the usual synthesis.

In carrying out the process according to the second aspect of this invention, the O-protected DL-3-(3,4-dihydroxyphenyl)serine of the formula (II) may be prepared through a usual synthetic route, for instance, by reacting 1 molar proportion of glycine with 2 molar proportions of 3,4-dihydroxybenzaldehyde of which the hydroxyl groups have been protected with a known group for protection of the phenolic hydroxyl group such as an aralkyl group, especially benzyl group, followed by hydrolysis of the reaction product under acidic conditions using e.g. a diluted hydrochloric acid (see J.C.S. pages 658–662 (1947)). The resulting O-protected DL-3-(3,4-dihydroxyphenyl)serine in the form of a mixture of threo- and erythro-isomers thereof may be isolated into the respective isomers according to any conventional isolation technique, e.g. by a fractional crystallization from a suitable organic solvent such as isopropanol.

The O-protected DL-threo-3-(3,4-dihydroxyphenyl)serine (II'Z) thus isolated may be converted in the step (a) of the present process into the corresponding N-benzyl derivative of the general formula (V):

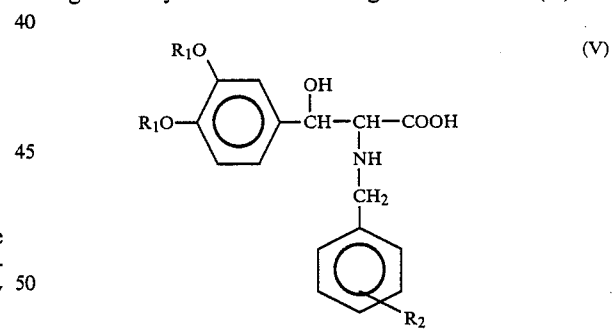
(V)

wherein $R_1$ and $R_2$ have the same meanings as defined above, for example, by reacting it with a benzaldehyde compound of the general formula (IV'):

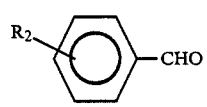
(IV')

wherein $R_2$ has the same meaning as defined above, to form an adduct of Schiff base type, followed by reducing the adduct with a reducing agent such as sodium borohydride or sodium cyanoborohydride in a suitable solvent such as an aqueous lower alkanol. When $R_1$ represents benzyl group and $R_2$ represents hydrogen, the resulting DL-threo-3-(3,4-dibenzyloxyphenyl)-N-benzylserine as a melting point of 183°–185° C. with decomposition. Corresponding erythro isomer may be derived from DL-erythro-3-(3,4-dibenzyloxyphenyl)-serine in the same manner as above for the threo isomer and has a melting point of 173°–174° C. with decomposition. The threo and erythro isomers so prepared find their IR and NMR spectra clearly different from each other.

heavy metal catalyst such as palladium on carbon. Various other deprotection methods well known in the art may, of course, be utilized for the final deprotection step (c) of the process according to this invention.

Melting point and NMR spectrum of DL-threo-3-(3,4-dihydroxyphenyl)-N-methylserine thus synthesized are given in Table 1 together with those of the corresponding erythro isomer.

TABLE 1

| | DL—3-(3,4-Dihydroxyphenyl)-N—methylserine | |
|---|---|---|
| Properties | Threo isomer | Erythro isomer |
| Melting point | 163–165° C. with decomposition | 221–223° C. with decomposition |
| NMR spectrum in Heavy water-Deutero-hydrochloric acid; External standard: TMS | δ 3.05 (s, 3H) <br> δ 4.57 (d, 1H, J=7Hz) <br> δ 5.52 (d, 1H) <br> δ 7.23–7.43 (3H) | δ 3.27 (s, 3H) <br> δ 4.73 (d, 1H, J=4Hz) <br> δ 5.77 (d, 1H) <br> δ 7.32–7.50 (3H) |

The N-methylation reaction of the N- and O-blocked DL-threo-3-(3,4-dihydroxyphenyl)serine of the general formula (V) may be effected by various known N-methylating techniques, thus yielding the N- and O-blocked DL-threo-3-(3,4-dihydroxyphenyl)-N-methylserine of the general formula (VI):

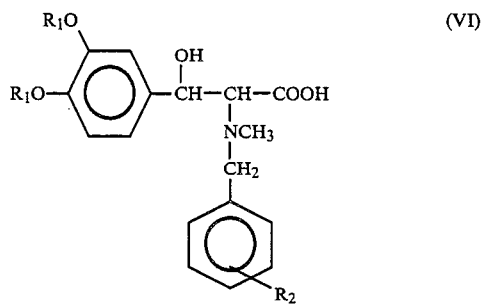

wherein $R_1$ and $R_2$ are as defined above. A preferred method for the N-methylation is to react the compound of the general formula (V) with formaldehyde in an inert solvent such as an aqueous alcohol, followed by the reduction with a reducing agent such as sodium cyanoborohydride and sodium borohydride. The use as reducing agent of sodium cyanoborohydride is optimum for the selective N-methylation in a high yield. When $R_1$ represents benzyl group and $R_2$ represents hydrogen, the resulting DL-threo-3-(3,4-dibenzyloxyphenyl)-N-benzyl-N-methylserine has a melting point of 133°–135° C. By way of reference, the corresponding erythro isomer has a melting point of 154°–156° C. with decomposition as well as IR and NMR spectra clearly different from those of the threo isomer.

The final step (c) for removal of the N,O-blocking groups from the N- and O-blocked DL-threo-3-(3,4-dihydroxyphenyl)-N-methylserine of general formula (VI) may be carried out by an appropriate method or methods, which is or are known per se, according to the nature of the O-protecting groups $R_1$, and the N-blocking benzyl group. A preferred method for the deprotection, when applied to the compound of formula (VI) where $R_1$ is benzyl and $R_2$ is hydrogen, comprises dissolving the compound (VI) in a solvent such as a lower alkanol, e.g. methanol, ethanol, propanol and butanol and a mixture thereof, or a mixture of water and one or more such lower alkanol and subjecting the resulting solution to catalytic hydrogenolysis in the presence of a Thus, the DL-threo- and erythro-3-(3,4-dihydroxyphenyl)-N-methylserines are clearly different from each other in their melting point and NMR spectrum as well as in their IR spectrum, and they are therefore concluded to be different substances.

Both the DL-threo- and erythro-3-(3,4-dihydroxyphenyl)-N-methyserines obtained as above are amphoteric substances and form salts with a variety of acids and bases. The salts so formed should also be included within this invention. Examples of such acids may include pharmaceutically acceptable inorganic acids such as sulfuric acid, hydrochloric acid and hydrobromic acid and pharmaceutically acceptable organic acids such as trifluoroacetic acid. Examples of such bases are pharmaceutically acceptable bases such as sodium hydroxide and potassium hydroxide.

As will be seen from the formula (I) given hereinbefore for 3-(3,4-dihydroxyphenyl)-N-methylserine, this compound contains two unsymmertical carbon atoms in the molecule thereof, so that theoretically, there exist four steric isomers, including the L-threo isomer, L-erythro isomer, D-threo isomer and D-erythro isomer.

We have considered that amongst the above-mentioned four isomers of 3-(3,4-dihydroxyphenyl)-N-methylserine, (that is, adrenalinecarboxylic acid), only L-threo-3-(3,4-dihydroxyphenyl)-N-methylserine, namely L-threo-adrenalinecarboxylic acid is most useful for therapeutic treatment of parkinsonism. In the course of our investigation on physiological and pharmacological activities of threo-adrenalinecarboxylic acids, therefore, we have made our effort to isolate the DL-threo-adrenalinecarboxylic acid into the separate L-form and D-form. As a result, we have now succeeded to provide L-threo-adrenalinecarboxylic acid separately from the D-isomer, and we have now confirmed that L-threo-adrenalinecarboxylic acid evidently exhibits antiparkinsonian activities and antidepressive activities and is useful in therapeutic treatment of parkinsonism and depression. L-Threo-adrenalinecarboxylic acid is of a low toxicity and shows remarkedly high pharmacological activities so that this compound is useful as a medicinal agent, and this compound is a novel one as it is not discribed in any literature.

Thus, according to this invention, there is firstly provided as the new compound L-threo-adrenalinecarboxylic acid, namely L-threo-3-(3,4-dihydroxyphenyl)-N-methylserine or a pharmaceutically acceptable salt or hydrate thereof. Hence, a pure chemical substance essentially consisting of L-threo-3-(3,4-dihydroxyphenyl)-N-methylserine now becomes available according to this invention.

The threo-3-(3,4-dihydroxyphenyl)-N-methylserine product obtained by the process according to the second aspect of this invention is in the DL-form, namely in the form of a mixture of the L-form and the D-form and may usually be in the form of a racemic mixture. Through our investigation, we have now discovered that L-threo-adrenalinecarboxylic acid can be obtained when the 2-amino group of the racemic or DL-threo-3-(3,4-dibenzyloxyphenyl)-N-methylserine synthetized as an intermediate in the aforesaid process of the second aspect invention or by a usual synthetic route is at first linked with such an N-blocking group, for example, p-methoxybenzyloxycarbonyl group, which is readily cleavable without affecting the benzyl groups of protecting the catechol moiety of the starting racemic or DL-compound, followed by reacting the resultant racemic or DL-threo-3-(3,4-dibenzyloxyphenyl)-N-p-methoxybenzyloxycarbonylserine with an optically active amine such as an optically active ephedrine, an optically active 2-amino-1,1-diphenyl-1-propanol, an optically active threo-1-(p-nitrophenyl)-2-amino-1,3-propanediol and the like to form a mixture comprising the salt of the D-serine compound with the optically active amine and the salt of the L-serine compound with the optically active amine, and further followed by isolating the amino salt of L-threo-3-(3,4-dibenzyloxyphenyl)-N-p-methoxybenzyloxycarbonyserine from the mixture of the amine salts of D- and L-threo-3-(3,4-dibenzyloxyphenyl)-N-p-methoxybenzyloxycarbonylserine through fractional recrystallization from an appropriate organic solvent with utilizing the difference in the solubilities of the amine salt of the D-serine compound and the amine salt of the L-serine compound. The L-threo-3-(3,4-dibenzyloxyphenyl)-N-p-methoxybenzyloxycarbonylserine obtained by the above-mentioned optical resolution method and the following extraction with organic solvent such as ethyl acetate under the acidic conditions is then hydrolyzed with a suitable acid such as hydrochloric acid to remove the p-methoxybenzyloxycarbonyl group threfrom and thereby to afford L-threo-(3,4-dibenzyloxyphenyl)serine, which is subsequently N-methylated by reacting with dimethyl sulfate in dry acetone in the presence of potassium carbonate, whereby L-threo-3-(3,4-dibenzyloxyphenyl)-N-methylserine methyl ester is formed. When this methyl ester is saponified under alkaline conditions, there is obtained L-threo-3-(3,4-dibenzyloxyphenyl)-N-methylserine. The latter compound can then be subjected to a deprotection reaction for the removal of the O-protecting benzyl groups to afford the desired L-threo-3-(3,4-dihydroxyphenyl)-N-methylserine, namely L-threo-adrenalinecarboxylic acid.

According to a third aspect of this invention, therefore, there is provided a process for the production of L-threo-3-(3,4-dihydroxyphenyl)-N-methylserine, which comprises the steps of:

(i) introducing an N-protecting group ($R_3$) which can readily be removed without involving cleavage of the O-protecting groups ($R_1$), into the 2-amino group of an O-protected DL-threo-3-(3,4-dihydroxyphenyl)serine derivative of the formula (II'):

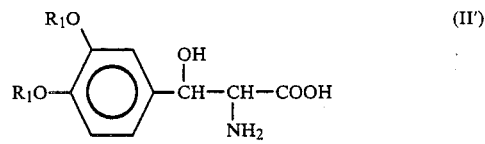

wherein $R_1$ denotes a group for protecting the phenolic hydroxyl group, to produce an N,O-protected DL-threo-3-(3,4-dihydroxyphenyl)serine derivative of the formula (VII):

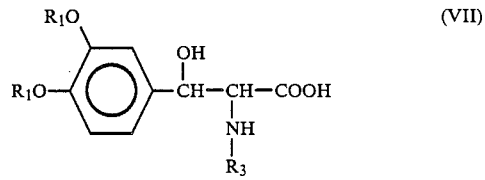

wherein $R_1$ and $R_3$ are as defined above, (ii) optically resolving said N,O-protected DL-threo-3-(3,4-dihydroxyphenyl)serine derivative by reacting the latter with an optically active amine and then fractionally recrystallizing the resultant amine salts of the N,O-protected DL-threo-3-(3,4-dihydroxyphenyl)serine derivative from such a suitable organic solvent in which the amine salt of the N,O-protected L-threo-3-(3,4-dihydroxyphenyl)serine derivative is soluble at a solubility different from that of the amine salt of the N,O-protected D-threo-3-(3,4-dihydroxyphenyl)serine derivative, whereby the amine salt of the N,O-protected L-threo-3-(3,4-dihydroxyphenyl)serine derivative is isolated from the mixture of the amine salts of the N,O-protected D- and L-threo-3-(3,4-dihydroxyphenyl)serine derivatives, (iii) removing the optically active amine component from the amine salt of the N,O-protected L-threo-3-(3,4-dihydroxyphenyl)serine derivative so isolated to yield the N,O-protected L-threo-3-(3,4-dihydroxyphenyl)serine derivative, (iv) removing the N-protecting group ($R_3$) from the 2-amino group of said N,O-protected L-threo-3-(3,4-dihydroxyphenyl)serine derivative, (v) reacting the resulting O-protected L-threo-3-(3,4-dihydroxyphenyl)serine derivative with dimethyl sulfate in anhydrous acetone in the presence of an anhydrous alkali metal carbonate to produce the O-protected L-threo-3(3,4-dihydroxyphenyl)-N-methylserine methyl ester, (vi) saponifying said methyl ester under alkaline conditions, and (vii) subjecting the O-protected L-threo-3-(3,4-dihydroxyphenyl)-N-methylserine obtained to a deprotecting reaction for removal of the O-protecting groups ($R_1$) therefrom, to afford the desired L-threo-3-(3,4-dihydroxyphenyl)-N-methylserine.

The process according to the above third aspect of this invention is now described in more details.

The O-protected DL-threo-3-(3,4-dihydroxyphenyl)serine derivative (II') which is used as the starting material in the present process may be prepared starting from glycine and the O-protected 3,4-dihydroxybenzaldehyde in the same way as described hereinbefore with regard to the process of the second aspect of this invention. A specific preferred example of this O-protected DL-threo-3-(3,4-dihydroxyphenyl)serine derivative (II') is DL-threo-3-(3,4-dibenzyloxyphenyl)serine.

In the step (i) of the present process, the reaction for introduction of the N-protecting group ($R_3$) into the 2-amino group of the starting compound (II') may be achieved by a conventional N-protecting method known in the usual synthesis of peptides. The N-protecting group ($R_3$) may suitably be such one which can readily be removed by hydrolysis under acidic conditions without involving undesired cleavage of the O-protecting group ($R_1$) for protecting the phenolic 3- and 4-hydroxyl groups present in the catechol moiety of the starting compound (II'). Preferred examples of the N-protecting group ($R_3$) include p-methoxybenzyloxycarbonyl and tert-butoxycarbonyl.

In the step (ii) of the present process, the optical resolution of the N,O-protected DL-threo-3-(3,4-dihydroxyphenyl)serine derivative (VII) so prepared may be conducted in various ways but may preferably be achieved according to a known fractional recrystallization method using e.g. racemic or DL-threo-3-(3,4-dibenzyloxyphenyl)-N-p-methoxybenzyloxycarbonylserine and by reacting the latter DL-serine compound with an equimolar or a smaller proportion of (−)-ephedrine as an optically active amine in solution in an appropriate organic solvent such as ehtanol, thereby preparing a homo-. geneous solution containing the salts of said DL-serine compound with the (−)-ephedrine dissolved therein, and then effecting the fractional recrystallizatioq by allowing said homogeneous solution to stand at such an appropriate temperature that the salt of the D-threo-3-(3,4-dibenzyloxyphenyl)-N-p-methoxybenzyloxycarbonylserine with (−)-ephedrine is preferentially deposited as crystals. When the (−)-ephedrine salt of the D-serine compound so deposited is then recrystallized once from methanol, it can be purified to an optically pure product. The (−)-ephedrine salt of the D-serine compound so purified may then be treated with an aqueous mineral acid such as aqueous hydrochloric acid, aqueous sulfuric acid, aqueous phosphoric acid and the like, followed by extracting the resulting solution in aqueous mineral acid with a water-immiscible organic solvent such as ethyl acetate, whereby the (−)-ephedrine component is removed from said (−)-ephedrine salt of the D-serine compound and D-threo-3-(3,4-dibenzyloxyphenyl)-N-p-methoxybenzyloxycarbonylserine is thus recovered into the solution (the extract) in the water-immiscible organic solvent.

For recovery of L-threo-3-(3,4-dibenzyloxyphenyl)-N-methoxybenzyloxycarbonylserine, the mother liquor from which the (−)-ephedrine salt of the D-serine compound deposited through the above-mentioned fractional recrystallization process has been removed is then acidified by addition of an aqueous mineral acid to remove the (−)-ephedrine component from the (−)-ephedrine salt of L-threo-3-(3,4-dibenzyloxyphenyl)-N-p-methoxybenzyloxycarbonylserine which is remaining dissolved in said mother liquor. The mother liquor so acidified is subsequently extracted with a water-immiscible organic solvent such as ethyl acetate to afford a solution (the extract) of L-threo-3-(3,4-dibenzyloxyphenyl)-N-p-methoxybenzyloxycarbonylserine. Alternatively, the aforesaid acidified mother liquor may be concentrated to dryness and the resulting solid residue may be dissolved in an organic solvent such as ethyl acetate, followed by washing the resultant organic solution with aqueous hydrochloric acid and then with water to give a partially purified organic solution of L-threo-3-(3,4-dibenzyloxyphenyl)-N-p-methoxybenzyloxycarbonylserine. An optically pure product of L-threo-3-(3,4-dibenzyloxyphenyl)-N-p-methoxybenzyloxycarbonylserine may be afforded by recrystallization twice from a mixture of ethyl acetate, isopropanol and petroleum ether.

While, when (+)-ephedrine, S-2-amino-1,1-diphenyl-1-propanol or L-threo-1-(p-nitrophenyl)-2-amino-1,3-propanediol and the like is employed as the optical resolution reagent in place of the (−)-ephedrine in the above-mentioned procedure, the salt of L-threo-3-(3,4-dibenzyloxyphenyl)-N-p-methoxybenzyloxycarbonylserine with (+)-ephedrine or the like is at first deposited as crystals from the organic solution, whereas the salt of D-threo-3-(3,4-dibenzyloxyphenyl)-N-p-methoxybenzyloxycarbonylserine with (+)-ephedrine is remaining dissolved in the mother liquor. The amine salt of the L-serine compound so deposited may be dissolved in aqueous mineral acid and the acidic solution obtained may be extracted with a water-immiscible organic solvent such as ethyl acetate to isolate L-threo-3-(3,4-dibenzyloxyphenyl)-N-p-methoxybenzyloxycarbonylserine.

As appropriate organic solvent for use in the above-mentioned optical resolution process, there may be employed various organic solvents of neutral nature, but not such organic solvents which would prevent the formation of the salt of the DL-serine compound with the optically active amine, for example, acidic organic solvents like to acetic acid, as well as basic organic solvents like to various amines. For sake of easy handability and low cost, it is desirable to use acetone, methylethyl ketone, methanol, ethanol, isopropanol, a mixture of one of these ketones or alcohols with water, or ethyl acetate, toluene, acetonitrile, dichloroethane, either alone or in mixture of two or more thereof.

The optical resolution process may be conducted at an appropriate temperature which may be ambient temperature or a lower temperature or a higher temperature. The organic solution containing the salts of the DL-serine compound with the optically active amine to be resolved optically may be heated to the boiling temperature of the organic solvent employed here, in order to provide an initially homogeneous solution system where the fractional recrystallization is to occur. The organic solution of the amine salts of the DL-serine compound may be cooled slowly in order to ensure that the amine salt of the D- or L-serine compound is crystallized out preferentially at a high purity. No critical requirement is involved in carrying out the optical resolution step of the present process.

In this way, there is obtained the N,O-protected L-threo-3-(3,4-dihydroxyphenyl)serine derivative, for example, L-threo-3-(3,4-dibenzyloxyphenyl)-N-p-methoxybenzyloxycarbonylserine from the steps (i) to (iii) of the present process as described above. In the subsequent step (iv) of the present process, the N,O-protected L-threo-3-(3,4-dihydroxyphenyl)serine derivative is hydrolyzed with a mineral acid such as hydrochloric, sulfuric or hydrobromic acid or with an organic acid such as trifluoroacetic acid in an organic solvent such as a lower alkanol, for example, methanol or propanol at or near ambient temperature in order to remove the N-protecting group ($R_3$) smoothly therefrom. Thus, the salt of the O-protected L-threo-3-(3,4-dihydroxyphenyl)serine with the mineral or organic acid employed is afforded, for example, the L-threo-3-(3,4-dibenzyloxyphenyl)serine hydrochloride.

In the step (v) of the present process, the O-protected L-threo-(3,4-dihydroxyphenyl)serine, for example, L-threo-3-(3,4-dibenzyloxyphenyl)serine is N-methylated in anhydrous acetone by reacting with dimethyl sulfate in the presence of an alkali metal carbonate such as potassium carbonate, so that the O-protected L-threo-3-(3,4-dihydroxyphenyl)-N-methylserine methyl ester, for example, the L-threo-3-(3,4-dibenzyloxyphenyl)-N-methylserine methyl ester is produced. This methyl ester, without being isolated, may be saponified under alkaline conditions in the further step (vi) of the present process, for example, by treating with an aqueous solution of an alkali metal hydroxide, preferably a 0.5 to 2N aqueous solution of an alkali metal hydroxide such as sodium hydroxide. In this way, the O-protected L-threo-3-(3,4-dihydroxyphenyl)-N-methylserine, for example, L-threo-3-(3,4-dibenzyloxyphenyl)-N-methylserine is afforded in a high yield.

In the above N-methylation step (v), the O-protected L-threo-3-(3,4-dihydroxyphenyl)serine may be used as such in the form of free amino acid but may preferably be employed in the form of its acid-addition salt with a mineral acid, for example, the hydrochloride, since it is ensured threby that the efficiency of the desired N-methylation can be increased sharply to about 90% with resulting in a remarkedly increased improvement of the yield of the desired N-methylserine product. The anhydrous alkali metal carbonate such as potassium carbonate may then be used in an amount of 2 to 10 moles, preferably 5 moles per 1 mole of the starting O-protected L-threo-3-(3,4-dihydroxyphenyl)serine. The N-methylating reagent, dimethyl sulfate may be employed in an amount of 2–10 moles, preferably 4 moles. The reaction temperature for N-methylation may be in the range of 0° to 50° C. and may preferably be at ambient temperature or thereabout. In this N-methylation step (v), the O-protected L-threo-3-(3,4-dihydroxyphenyl)serine to be N-methylated is sparingly soluble in the dry acetone, the N-methylation reaction proceeds in a heterogeneous reaction system, and the desired N-methylation cannot take place if there is employed any organic solvent other than the dry acetone. This suggests that the acetone takes a part in achieving the desired mono-N-methylation at the 2-amino group of the O-protected L-threo-3-(3,4-dihydroxyphenyl)serine, which is our new finding.

In the final step (vii) of the present process, the O-protected L-threo-3-(3,4-dihydroxyphenyl)-N-methylserine obtained as above, for example, L-threo-3-(3,4-dibenzyloxyphenyl)-N-methylserine, as the saponification product from the step (vi) of the process, is then subjected to a known deprotecting reaction for removal of the O-protecting groups ($R_1$), for example, the benzyl groups. The reaction for the deprotection may be accomplished according to the nature of the O-protecting groups ($R_1$) and in a manner known in the conventional synthesis. When the O-protecting groups ($R_1$) are of an aralkyl type, such as benzyl, the deprotecting reaction may be achieved by a conventional, catalytic hydrogenolysis with gaseous hydrogen at an atmospheric pressure or at a higher pressure in the presence of a nobel metal catalyst such as platinum-on-carbon or palladium-on-carbon. For this catalytic hydrogenolysis, it is preferred to use a lower alkanol solvent such as methanol, ethanol and the like or a mixture of one of these alkanols with water as the reaction medium. The hydrogenolysis usually may be conducted at a temperature in the vicinity of ambient temperature but may, in general, be carried out at any temperature of from 0° C. to 80° C. Further, it is desirable that 0.8 to 20 moles of an acid is added to the reaction mixture for the hydrogenolysis for the purpose of promoting the hydrogenolysis reaction or for the purpose of enhancing the solubility of the desired reaction product in the reaction solution. Preferred examples of the acid to be added for this purpose include a mineral acid such as hydrochloric and sulfuric acids, as well as an organic acid such as acetic and methanesulfonic acids, and the like. After the hydrogenolysis reaction is finished, the reaction mixture is filtered to remove the catalyst, and the filtered reaction mixture is concentrated to crystallize out the desired L-threo-3-(3,4-dihydroxyphenyl)-N-methylserine, namely L-threo-adrenalinecarboxylic acid. In case the reaction mixture has been acidified by the addition of acid, the reaction mixture is neutralized by addition of an alkali before it is concentrated to effect the crystallization of the desired L-threo-adrenalinecarboxylic acid.

As described hereinbefore, the N-methylation step of the process of the third aspect of this invention involves our new finding which we cannot predict from our previous knowledge of N-methylation of amino group. According to a fourth, broader aspect of this invention, there is provided a process for the production of L-threo-3-(3,4-dihydroxyphenyl)-N-methylserine, which comprises the steps of:

(a) reacting an O-protected L-threo-3-(3,4-dihydroxyphenyl)serine derivative of the formula (II")

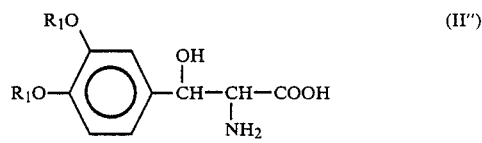

wherein $R_1$ is a group for protecting the phenolic hydroxyl group and preferably is an aralkyl group, in suspension in anhydrous acetone with dimethyl sulfate in the presence of an anhydrous alkali metal carbonate, to produce the O-protected L-threo-3-(3,4-dihydroxyphenyl)-N-methylserine methyl ester, (b) saponifying said methyl ester under alkaline conditions, and (c) subjecting the O-protected L-threo-3-(3,4-dihydroxyphenyl)-N-methylserine obtained to a known deprotecting reaction for removal of the O-protecting group ($R_1$) therefrom, to afford the desired L-threo-3-(3,4-dihydroxyphenyl)-N-methylserine.

The L-threo-3-(3,4-dihydroxyphenyl)-N-methylserine obtained by the process of the third or fourth aspect of this invention is an amphoteric substance just like to the racemic or DL-product as obtained by the process of the second aspect of this invention, so that it may be converted into its salt by reacting with acid or base in the same way as described with regard to the second aspect of this invention.

The threo-3-(3,4-dihydroxyphenyl)-N-methylserine, either in the DL-form or in the L-form as obtained according to this invention exhibits antiparkinsonian activity and antidepressive activity as described hereinbefore. Particularly, we have now found that L-threo-3-(3,4-dihydroxyphenyl)-N-methylserine, that is, L-threo-adrenalinecarboxylic acid as administered intraperitoneally or intravenously can penetrate through the blood-brain barrier into the brain and can increase the concentration or level of adrenaline in the brain through non-elucidated biological mechanism, though L-threo-adrenalinecarboxylic acid itself is not decarboxylated into adrenaline by actions of the enzymes present in the homogenate of the whole brain and that L-threo-adrenalinecarboxylic acid is able to exert different biological and physiological activities on the nerve system, and hence the L-threo-adrenalinecarboxylic acid especially can exhibit remarkably high antiparkinsonian activity and antidepressive activity. Furthermore, the fact that L-threo-adrenalinecarboxylic acid of this invention is able to penetrate and transfer through the blood-brain barrier into the brain of a living animal when it is intraperitoneally or intravenously administered is to be compared with that the known L-threo-(3,4-dihydroxyphenyl)serine (DOPS) does not. And it is also to be noticed that neither adrenaline, nor noradrenaline is able to penetrate through the blood-brain barrier into the brain.

According to a fifth aspect of this invention, therefore, there is provided a pharmaceutical composition comprising as the active ingredient an effective amount of L-threo-3-(3,4-dihydroxyphenyl)-N-methylserine or a pharmaceutically active salt or hydrate thereof, in association with a pharmaceutically acceptable carrier or vehicle for the active ingredient.

According to another aspect of this invention, there is provided a method of therepeutically treating parkinsonism which comprises administering to the patient an effective amount of L-threo-3-(3,4-dihydroxyphenyl)-N-methylserine or a pharmaceutically acceptable salt or hydrate thereof. There is also provided a method of therapeutically treating mental depression disease which comprises administering to the patient an effective amount of L-threo-3-(3,4-dihydroxyphenyl)-N-methylserine or a pharmaceutically acceptable salt or hydrate thereof.

The active compound according to this invention may be formulated into the form of pharmaceutical compositions with one or more pharmaceutically acceptable carriers or excipients. Examples of such carriers may be organic and inorganic inert carrier materials suitable for oral and parenteral administrations such as water, gelatine, lactose, starch magnesium stearate, talc, vegitable oil, acasia gum, polyalkyleneglycol and yellow soft paraffin. The pharmaceutical compositions may be in the form of solid formulations such as tablet, suger-coated tablet, suppository and capsule or in the form of liquid formulations such as solution, suspension and emulsion. The pharmaceutical compositions may be in sterile state and may contain a conventional adjuvant such as preservatives, stabilizers, wetting agent or emulsifying agents, isotonizers and buffering agents. The pharmaceutical composition of this invention may contain an amount of, for example, 10% to 90% by weight of L-threo-3-(3,4-dihydroxyphenyl)-N-methylserine or a pharmaceutically acceptable salt or hydrate thereof. The dose of L-threo-3-(3,4-dihydroxyphenyl)-N-methylserine to be given to the patient may vary depending on symptoms of the disease, age of the patient and other various factors, and only for a guideline, a usual dosage of L-threo-3-(3,4-dihydroxyphenyl)-N-methylserine is 10 mg to 2000 mg for adult once daily.

Following Examples illustrate the production of the compound of this invention and of the starting and intermediate compounds thereof, but in no way limit this invention. The production of the corresponding erythro isomer is also given by way of reference.

EXAMPLE 1

Preparation of DL-threo-adrenalinecarboxylic acid (a) An aqueous solution (10 m)) containing glycine (2.4 g) and sodium hydroxide (3.21 g) was added at once to a suspension of 3,4-dibenzyloxybenzaldehyde (20.4 g) in ethanol (83 ml) at ambient temperature under vigorous stirring. The mixture was heated on a water bath in such a manner that the bath temperature was raised up to 77° C. over about 15 minutes, at which the solution became transparent, so that the heating was ceased immediately. The resulting solution was allowed to cool to 37° C. under stirring over about 1 hour, when a semi-oily deposit was formed. To this was added dropwise a 2N hydrochloric acid (75 ml) over about 15 minutes while the temperature in the mixture was carefully kept below 37° C., during which the deposit disappeared with the formation of a suspension. It was believed that in the above-mentioned operations, there occurred a series of reactions that one mole of glycine was first reacted with one mole of the benzaldehyde compound to form a Schiff base-type compound which was then reacted with another mole of the benzaldehyde compound according to aldol condensation, followed by being hydrolyzed with the hydrochloric acid, whereby yielding 3-(3,4-dibenzyloxyphenyl)serine.

The resulting suspension was stirred for further 3 hours at ambient temperature and then filtered. The filter cake was washed with a mixture of 3N hydrochloric acid (5 ml) and ethanol (5 ml) and the washings were collected and combined with the filtrate, to which was then slowly added sodium acetate trihydrate (11.5 g) at ambient temperature under stirring, during which the amino acid gradually started precipitating out. The reaction mixture was allowed to stand under ice-cooling for 2 days and then filtered to recover the amino acid as crude crystals. The crystals so recovered was washed with water (20 ml) and slowly added to a mixture of water (40 ml), concentrated hydrochloric acid (2.5 ml) and ethanol (60 ml) at room temperature under stirring. A transparent solution was obtained, after which activated carbon (1.5 g) was added thereto and the mixture was stirred at room temperature for 20 minutes and then filtered. To the filtrate was slowly added diethylamine (about 3 ml to adjust the pH to 4.0, resulting in the gradual precipitation of the amino acid. The mixture was allowed to stand at 0° C. overnight and then filtered to recover the crystals which were dried over phosphorus pentoxide in vacuo overnight, yielding a mixture of DL-threo-3-(3,4-dibenzyloxyphenyl)serine and DL-erythro-3-(3,4-dibenzyloxyphenyl)serine. Yield 3.89 g; This mixture showed a melting point of 138° C. (b) The mixture of DL-threo- and DL-erythro-3-(3,4-dibenzyloxyphenyl)serines (1.4 g) obtained in the step (a) above was dissolved in a mixture of ethanol (8.4 ml) and 3N hydrochloric acid (2.8 ml). The solvent used was distilled off in vacuo and the residue was washed well with diethylether and dried to afford the corresponding hydrochlorides (1.5 g).

The mixture of DL-threo-/DL-erythro-3-(3,4-dibenzyloxyphenyl)serines in the form of their hydrochloride so produced (1.5 g) was recrystallized from isopropanol, giving crystals of DL-threo-3-(3,4-dibenzyloxyphenyl)serine hydrochloride (0.846 g). Melting point 145°-149° C.

The mother liquor was concentrated in vacuo and the precipitate so formed was filtered to afford crystals of DL-erythro-3-(3,4-dibenzyloxyphenyl)serine hydrochloride (0.327 g). Melting point 130°–137° C.

(c) DL-threo-3-(3,4-dibenzyloxyphenyl)serine hydrochloride (21.0 g) obtained in the step (b) above was dissolved in a mixture of methanol (500 ml) and water (250 ml). To the resulting solution, benzaldehyde (16.0 g) and 1N aqueous sodium hydroxide solution (150 ml) were added under stirring and ice-cooling, and the mixture was stirred at room temperature for 3 hours to conduct the condensation reaction Subsequently, sodium borohydride (5.70 g) was slowly added to the reaction mixture over 15 minutes under stirring and ice-cooling, and then the mixture was stirred at room temperature for further 1 hour to effect the reducing reaction. After the reaction solution was again ice-cooled, acetic acid was added thereto to decompose the excess sodium borohydride used and to neutralize the mixture, thus forming a precipitate. The stirring and ice-cooling were continued for further 2 hours, after which the precipitate thus formed was recovered by filtration, washed with water and then with methanol and dried in vacuo to give DL-threo-3-(3,4-dibenzyloxyphenyl)-N-benzylserine (21.0 g) as a white powder.

Melting point: 173°–174° C. with decomposition
Elemental analysis: Calculated for $C_{30}H_{29}O_5N$: C 74.53, H 6.00, N 2.90%; Found: C 74.25, H 6.09, N 2.74%

(d) DL-threo-3-(3,4-dibenzyloxyphenyl)-N-benzylserine (10.0 g) obtained in the step (c) above was suspended in a 75% aqueous ethanol (300 ml). To the suspension were added 1N aqueous sodium hydroxide solution (60 ml) and a 37% aqueous formalin solution (4.8 ml) under stirring, and the resulting mixture was further stirred at room temperature for 3 hours to conduct the reaction, giving a transparent solution. Then, sodium cyanoborohydride (3.80 g) was added and the mixture was stirred for 1 hour to conduct the reducing reaction. The reaction solution was ice-cooled and acidified with acetic acid to make the desired product precipitated. The stirring under ice-cooling was continued for further 2 hours to complete the precipitation and the resulting precipitate was recovered by filtration, washed with water and methanol in order and dried in vacuo, yielding DL-threo-3-(3,4-dibenzyloxyphenyl)-N-benzyl-N-methylserine.(9.05 g) as white crystals.

Melting point: 133°–135° C.
Elemental analysis: Calculated for $C_{31}H_{31}O_5N$: C 74.85, H 6.24, N 2.82%; Found: C 74.79, H 6.22, N 2.70%

(e) DL-threo-3-(3,4-dibenzyloxyphenyl)-N-benzyl-N-methylserine (5.00 g) obtained in the step (d) above was dissolved in a mixture of acetic acid (150 ml) and ehtanol (150 ml), and 10% palladium-carbon (1.50 g) was added to the solution. The hydrogenolysis (for the removal of benzyl groups) was effected by stirring the resulting mixture at room temperature under a stream of hydrogen gas for 3 hours. The reaction mixture was filtered to remove the catalyst and the filtrate was concentrated in vacuo. The residue was dissolved in methanol (50 ml) and the resultant solution was allowed to stand for the crystallization of the desired product. The crystals thus deposited was filtered and dried in vacuo, yielding the crude product (2.12 g). Recrystallization of the crude product from 50% aqueous methanol gave DL-threo-3-(3,4-dihydroxyphenyl)-N-methylserine, i.e. DL-threo-adrenalinecarboxylic acid.

Melting point 163°–165° C. (with decomposition)

NMR spectrum (δ values; deutero-water-deuterohydrochloric acid; TMS as external standard): 3.05 (s, 3H), 4.57 (d, 1H, J=7 Hz), 5.52 (d, 1H), 7.23–7.42 (m, 3H)

Elemental analysis: Calculated for $C_{10}H_{13}O_5N \cdot H_2O$: C 48.99, H 6.21, N 5.71%; Found: C 48.91, H 6.24, N 5.54%

EXAMPLE 2

Preparation of L-threo-adrenalinecarboxylic acid (a) The amino group of DL-threo-3-(3,4-dibenzyloxyphenyl)serine obtained in Example 1 (b) above was protected with p-methoxybenzyloxycarbonyl group by reacting it with N-p-methoxybenzyloxycarbonyloxysuccinimide of the formula:

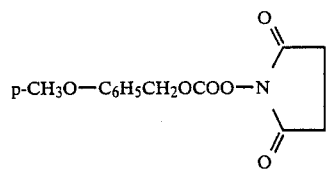

in a usual manner. The resulting DL-threo-3-(3,4-dibenzyloxyphenyl)-N-p-methoxybenzyloxycarbonylserine (20 g) was dissolved in ethanol (380 ml) and optically active (−)-ephedrine (4.19 g, 0.7 equivalent) was added to the solution. The resulting mixture which was a solution containing the salts of the DL-serine compound with (−)-ephedrine was allowed to stand at room temperature for 3 days, during which optical resolution took place due to the difference in the solubility of the salts. The crystals thus deposited were recovered by filtration and washed with ethanol, followed by recrystallization from a mixture of methanol and chloroform (2:1 by volume) two times, to yield the salt of D-threo-3-(3,4-dibenzyloxyphenyl)-N-p-methoxybenzyloxycarbonylserine with (−)-ephedrine (8.6 g).

Melting point 170°–171° C.
$[\alpha]_D^{26}$: −35° (c 1.0, dimethylformamide)
Elemental analysis: Calculated for $C_{42}H_{46}N_2O_9$: C 69.79, H 6.41, N 3.88%; Found: C 69.78, H 6.48, N 3.72%

On the other hand, the mother liquor, that is, the filtrate derived from the filtration step above by which said crystals of the D-threo compound were removed therefrom was concentrated to dryness. The resulting residue comprising the salt of L-threo-3-(3,4-dibenzyloxyphenyl)-N-p-methoxybenzyloxycarbonylserine with (−)-ephedrine was dissolved in ethyl acetate (100 ml) and the solution was washed with 3N hydrochloric acid (60 ml) for the removal of the ephedrine component. The ethyl acetate layer separated was washed with water (30 ml) and the water-washings were extracted with ethyl acetate (100 ml). The ethyl acetate layers were combined, dried over anhydrous sodium sulfate and concentrated to dryness. Recrystallization of the residue from a mixture of chloroform and hexane two times afforded L-threo-3-(3,4-dibenzyloxyphenyl)-N-p-methoxybenzyloxycarbonylserine (7.54 g).

Melting point: 129.5°–131.0° C.
$[\alpha]_D^{27}$: −17° (c 0.91, chloroform-methanol=10:1)
Elemental analysis: Calculated for $C_{32}H_{31}NO_8$: C 68.93, H 5.60, N 2.51%; Found: C 68.71, H 5.62, N 2.40%

(b) The salt of D-threo-3-(3,4-dibenzyloxyphenyl)-N-p-methoxybenzyloxycarbonylserine with (−)-ephedrine (8.6 g) obtained as above was added to a mixture of ethyl acetate (100 ml) and 3N hydrochloric acid (60 ml) to effect extraction of the free acid compound. The ethyl acetate layer separated was washed with 3N hydrochloric acid (60 ml) and then with water (30 ml), and the water-washings were extracted with ethyl acetate (100 ml). The ethyl acetate layers were combined and dried over anhydrous sodium sulfate and concentrated to dryness. The resulting solid residue was recrystallized from a mixture of chloroform and hexane to yield D-threo-3-(3,4-dibenzyloxyphenyl)-N-p-methoxybenzyloxycarbonylserine (6.35 g).

Melting point: 130.5°–131.5° C.

$[\alpha]_D^{25}$: +18° (c 0.91, chloroform-methanol = 10:1)

Elemental analysis: Calculated for $C_{32}H_{31}NO_8$: C 68.93, H 5.60, N 2.51%; Found: C 68.98, H 5.67, N 2.40%

(c) L-threo-3-(3,4-dibenzyloxyphenyl)-N-p-methoxybenzyloxycarbonylserine (4.7 g) obtained in the step (a) above was dissolved in isopropanol (180 ml) and concentrated hydrochloric acid (18 ml) was added to the solution. The resulting solution was allowed to stand overnight at room temperature to effect hydrolysis (i.e. for the removal of the N-protecting p-methoxybenzyloxycarbonyl group). The reaction mixture was concentrated in vacuo to a volume of about 100 ml and then stirred under ice-cooling for 3 hours. The crystals so deposited were recovered by filtration and dried in vacuo to afford L-threo-3-(3,4-dibenzyloxyphenyl)serine hydrochloride (3.0 g; yield 83%).

Melting point: 148.5°–151° C.

$[\alpha]_D^{27}$: −5.3° (c 1.0, ethanol)

Elemental analysis: Calculated for $C_{23}H_{23}NO_5 \cdot HCl$: C 64.26, H 5.67, N 3.26%; Found: C 64.29, H 5.63, N 3.16%

(d) L-threo-3-(3,4-dibenzyloxyphenyl)serine hydrochloride (6.74 g) obtained in the step (c) above was suspended in dry acetone (52 ml) at room temperature and anhydrous potassium carbonate (10.8 g) was added to the suspension. After the resultant mixture was stirred at room temperature for about 10 minutes, dimethyl sulfate (5.93 ml) was added thereto, and the whole mixture (in the form of a suspension) was stirred overnight at room temperature to conduct the N-methylating reaction, whereby to give L-threo-3-(3,4-dibenzyloxyphenyl)-N-methylserine methyl ester. The reaction mixture was filtered to remove the anhydrous potassium carbonate which was washed with acetone. The filtrate and the acetone-washings were combined together and 1N hydrochloric acid (52 ml) was added thereto. The resultant mixture was stirred at room temperature for 75 minutes. The reaction mixture containing L-threo-3-(3,4-dibenzyloxyphenyl)-N-methylserine methyl ester was filtered and the filtrate was distilled in vacuo below 30° C. to remove the acetone. The residue was admixed with ethanol (54 ml) and 4N aqueous sodium hydroxide (27 ml), and the admixture was stirred at room temperature for about 30 minutes to effect the saponification, and then the reaction mixture was neutralized with 1N hydrochloric acid under ice-cooling to adjust the pH to 5–6, when crystals were deposited. The crystals were recovered by filtration and dried in vacuo to afford L-threo-3-(3,4-dibenzyloxyphenyl)-N-methylserine (6.05 g; yield 95%).

Melting point: 162°–164° C. $[\alpha]_D^{27}$: +8 0° (c 1.0, ethanol-1N HCl = 1:1)

Elemental analysis: Calculated for $C_{24}H_{25}NO_5$: C 70.74, H 6.18, N 3.44%; Found: C 70.26, H 6.20, N 3.24%

(e) L-threo-3-(3,4-dibenzyloxyphenyl)-N-methylserine (1.53 g) obtained in the step (d) above was suspended in an ethanol solution (3.1 ml) containing 10% concentrated hydrochloric acid. The suspension, after the addition of 10% palladium-carbon (150 mg), was stirred overnight in a stream of hydrogen at room temperature and atmospheric pressure to effect hydrogenolysis reaction (i.e. for the removal of the O-protecting benzyl groups). The reaction mixture was filtered to remove the catalyst and the filtrate was neutralized with an ethanolic solution containing 40% diethylamine under ice-cooling. The mixture was allowed to stand at −15° C. for 3 hours, then filtered, washed with a small volume of ethanol and dried to give L-threo-3-(3,4-dihydroxyphenyl)-N-methylserine, i.e. L-threo-adrenalinecarboxylic acid (850 mg). This was recrystallized from water (8.5 ml) containing ascorbic acid (1.7 mg) to yield L-threo-adrenalinecarboxylic acid in pure state (611 mg, yield 72%).

Melting point: 205°–208° C. with decomposition $[\alpha]_D^{27}$: −18° (c 1.0, 1N hydrochloric acid)

Elemental analysis: Calculated for $C_{10}H_{13}NO_5 \cdot \frac{1}{4}H_2O$: C 51.83, H 5.87, N 6.04%; Found: C 52.23, H 5.90, N 5.92%

According to the screening test described in the Japanese medical book "YAKUHIN KAIHATSU KISO KOZA" (V) 6. "YAKKO NO HYOKA (1)", "YAKURI SHIKEN HO", Volume "Jo", pages 175-177 (published by CHIJIN SHO I-N, Tokyo, 1971), it is considered that such a substance which exhibits an inhibitory activity against harmaline-induced tremor and also an inhibitory activity against reserpine-induced decrease in the body temperature of mice is useful as anti-parkinsonian agent and antidepressive agent. It is known that reserpine is active to induce an exhaustion of catecholamine in the nerve ending due to release of catecholamine involved threre and that administration of reserpine induces not only a decrease in the body temperature and a decrease in the blood pressure, but also various symptoms of Parkinson's disease such as Parkinson's facies, rigidity and tremor, as well as heavy depression conditions. For these reasons, it is presumed that such a compound exhibiting an anti-reserpine activity is useful not only as antidepressive drug but also as antiparkinsonian drug. From animal tests, we have now found that the DL- or L-threo-3-(3,4-dihydroxyphenyl)-N-methylserine according to this invention exhibit a higher anti-harmarine activity and a higher anti-reserpine activity, as compared to the known L-threo-3-(3,4-dihydroxyphenyl)serine (L-threo-DOPS). Accordingly, we take it that the DL- or L-threo-3-(3,4-dihydroxyphenyl)-N-methylserine, that is, DL- or L-threo-adrenalinecarboxylic acid is very promising as antiparkinsonian agent and also as antidepressive agent.

The physiological and pharmacological activities of DL- or L-threo-3-(3,4-dihydroxyphenyl)-N-methylserine (hereinafter referred to as DL- or L-threo-adrenalinecarboxylic acid) were assessed in the following tests.

Test 1

This test was made according to one usual method for screening antiparkinsonian drugs which determines inhibitory activity against harmaline-induced tremor.

ddY-strain Mice (male, body weight 20-30 g, five in each group) were used as test animal for respective tests. The new compound, DL-threo-adrenalinecarboxylic acid according to this invention, was intraperitoneally administered to each of the mice at a dosage of 400 mg/kg or 600 kg/kg, and after the lapse of 30 minutes harmaline was also intrapenitoneally injected to the same mice at a dosage of 10 mg/kg. Then, the duration of tremor action as induced in the mice under test was observed and recorded. The rate (percentage) of reduction in the duration of tremor action in relation to the control group of mice to which only harmaline was administered in the same dosage was calculated by the equation given below. By way of comparison DL-threo-3-(3,4-dihydroxyphenyl)serine (i.e. DL-threo-DOPS) in a dosage of 400 mg/kg was tested in the same manner as above.

Reduction (%) =

$$\frac{\left(\begin{array}{c}\text{Duration of tremor}\\\text{action in the}\\\text{control group}\end{array}\right) - \left(\begin{array}{c}\text{Duration of tremor}\\\text{action in the}\\\text{treated group}\end{array}\right)}{\left(\begin{array}{c}\text{Duration of tremor action in the}\\\text{control group}\end{array}\right)} \times 100$$

The results of this test are shown in Table 2 below.

TABLE 2

| Test compound | (Dosage) | Reduction (%) |
|---|---|---|
| Harmaline (10 mg/kg) | (Control) | 0 |
| DL—Threo-DOPS (400 mg/kg) + Harmaline (10 mg/kg) | (Comparison) | 26 |
| DL—Threo-adrenalinecarboxylic acid (400 mg/kg) + Harmaline (10 mg/kg) | (This invention) | 34 |
| DL—Threo-adrenalinecarboxylic acid (600 mg/kg) + harmaline (10 mg/kg) | (This invention) | 37 |

These results demonstrate that DL-threo-adrenalinecarboxylic acid is significantly superior to DL-threo-DOPS in respect of the reduction in duration of tremor action and may be useful as antiparkinsonian drug.

Test 2 ddY-strain Mice (male, body weight 20-30 g, five in each group) were used as the test animal for respective tests. Reserpine was intraperitoneally administered to each mouse at a dose of 4 mg/kg. 24 Hours later, the decreased body temperature of the mice was observed and recorded. After this, 1500 mg/kg or 2000 mg/kg of DL-threo-adrenalinecarboxylic acid was intraperitoneally administered to each of the mice having received reserpine. At the end of 1 hour and at the end of 2 hours after the administration of the DL-threo-adrenalinecarboxylic acid, the body temperature of these treated mice was determined and shown in Table 3 below. The results of Table 3 show that the DL-threo-adrenalinecarboxylic acid inhibited the reserpine-induced decrease in the body temperature of the treated mice, as compared to the control mice which had received reserpine but not the DL-threo-adrenalinecarboxylic acid, revealing that DL-threo-adrenalinecarboxylic acid of this invention is useful as antidepressive agent.

TABLE 3

| | Body Temperature (°C.) | |
|---|---|---|
| Test Compound (dosage) | 1 Hour after | 2 Hours after |
| Reserpine (4 mg/kg) (Control) | 30.9 | 30.5 |
| Reserpine (4 mg/kg) + DL—threo-adrenalinecarboxylic acid (1500 mg/kg) | 32.9 | 32.6 |
| Reserpine (4 mg/kg) + DL—threo-adrenalinecarboxylic acid (2000 mg/kg) | 34.0 | 32.5 |

Test 3

To ddY-strain mice (male, body weight 20-30 g, five in each group) was subcutaneously administered reserpine at a dose of 2.5 mg/kg. 24 Hours later, the decreased body temperature of the mice was determined and recorded. After this, 800 mg/kg of L-threo-adrenalinecarboxylic acid or 800 mg/kg of D-threo-adrenalinecarboxylic acid or DL-threo-adrenalinecarboxylic acid synthetized according to this invention was intraperitoneally administered to the mice having received reserpine. One hour after the administration of the threo-adrenalinecarboxylic acid, the body temperature of the treated mice was determined. Estimation was also made about whether the muscular rigidity as induced by reserpine was improved by the administration of the threo-adrenalinecarboxylic acid of this invention. The results of these tests are summarized in Table 4 below.

TABLE 4

| | Body Temperature (°C.) (Average ± Standard deviation) | | | |
|---|---|---|---|---|
| Test Compound (dosage) | Before administration of reserpine | 24 Hours after administration of reserpine | 1 Hour after administration of adrenaline carboxylic acid | Muscular Rigidity* |
| Control | 38.9 ± 0.2 | 34.7 ± 1.3 | 35.1 ± 0.9 | 0/5 |
| L—threo-adrenaline-carboxylic acid (800 mg/kg) | 39.0 ± 0.2 | 35.4 ± 0.4 | 38.7 ± 0.5 | 5/5 |
| D—threo-adrenaline-carboxylic acid (800 mg/kg) | 38.9 ± 0.2 | 36.0 ± 0.5 | 35.9 ± 0.5 | 0/5 |
| DL—threo-adrenaline-carboxylic acid (800 mg/kg) | 39.1 ± 0.2 | 34.9 ± 0.7 | 36.9 ± 0.3 | 0/5 |

Note:
The asterisk * denote the number of mice exhibiting significant improvement in the muscular rigidity per the total number of mice in each group under test.

As will be clear from the results of Table 4, L-threo-adrenalinecarboxylic acid remarkably inhibits the reserpine-induced decrease in the body temperature of mice and it also remarkably improves (eliminates or weakens) the muscular rigidity which is a main symptom of Parkinson's disease, demonstrating that the L-threo-adrenalinecarboxylic acid according to this invention is valuable as antidepressive agent and also as antiparkinsonian agent.

Test 4

This test is carried out to examine acute toxicity of the DL-threo-adrenalinecarboxylic acid.

To DDB4-strain mice (male, body weight 23-28 g, six in each group) was intraperitoneally administered at a dosage of 0.5 ml per mouse a suspension containing 20 mg/ml of DL-threo-adrenalinecarboxylic acid dispersed in an aqueous solution of 0.5% carboxymethylcellulose (CMC). The mice were then raised under normal conditions for 7 days after the administration of the compound. During these 7 days, the mice were observed and estimated with regard to their body weight, the quantity of feedstock and the quantity of water which were taken by the mice. No diference could be detected for these parameters between the treated group of the threo-adrenalinecarboxylic acid-receiving mice and the control group of the mice receiving no threo-adrenalinecarboxylic acid. The mice were further anatomically examined, the weights of substantial organs were measured, and bio-chemical tests of blood and tissue-pathological tests were conducted, revealing that no significant difference existed between the treated group of mice and the control group of mice in these respects.

Test 5

To mice (male, body weight 20–30 g, five in each group) was intraperitoneally administered 500 mg/kg of DL-threo-adrenalinecarboxylic acid of this invention or 500 mg/kg of DL-threo-DOPS (i.e., DL-threo-3-(3,4-dihydroxyphenyl)-serine). 90 Minutes after the i.p. administration, the whole brain portion was removed surgically from the mice. The quantity of the threo-adrenalinecarboxylic acid or the quantity of the threo-DOPS which was transferred into and accumulated in the brain portion of mice, as well as the quantity of adrenaline in the brain portion of mice were determined by a high-performance liquid chromatography. The results obtained are shown in Table 5 below.

TABLE 5

| Compound administered | Quantity (as average) of the administered compound present in brain | Quantity (as average) of adrenaline in brain |
|---|---|---|
| DL—threo-adrenalinecarboxylic acid | 2.0 n mole/g | 0.44 n mole/g |
| DL—threo-DOPS | Not detectable | Not tested |
| Not administered | Not detectable | 0.37 n mole/g |

In view of the results of the above Test 5, we initially interpreted that the L-isomer present in the DL-threo-adrenalinecarboxylic acid under test could penetrate and transfer through the blood-brain barrier into the brain to give the detected quantity of the threo-adrenalinecarboxylic acid in the brain, that the L-threo-adrenalinecarboxylic acid would be decarboxylated in vivo to give the detected quantity of adrenaline in the brain, and that the L-isomer present in the DL-threo-DOPS under test could not penetrate through the blood-brain barrier into the brain. From our recent researches as detailed in Test 6 and Test 7 described below, however, we have now discovered that our initial interpretation that L-threo-adrenalinecarboxylic acid as administered intraperitoneally or intravenously penetrates through the blood-brain barrier into the brain should be supportable now, whereas our initial interpretation that L-threo-adrenalinecarboxylic acid would be decarboxylated into adrenaline in vivo is not supported by the experimental data and is wrong. We now continue our research to elucidate why the quantity of adrenaline in the brain can be increased by intraperitoneal or intravenous injection of L-threo-adrenalinecarboxylic acid which is not decarboxylated in vitro.

Test 6

To mice of C57 Black-strain (male, 6-weeks-aged, body weight of 18–20 g, five in each group) was intravenously administered 1 mg/kg (4.125 $\mu$Ci/20 ng/0.2 ml/mouse), 10 mg/kg (4.125 $\mu$Ci/200 $\mu$g/0.2 ml/mouse), or 100 mg/kg (4.125 $\mu$Ci/2000 $\mu$g/0.2 ml/mouse) of radioactively labelled ($^{14}$C)-L-threo-adrenalinecarboxylic acid. Heparin (blood anticoagulant) at a dosage of 80 units/mouse was given intravenously to the treated mice at the times of 0.25 hours, 0.5 hours, 1 hour, 2 hours, 4 hours, 8 hours and 24 hours after the administration of L-threo-adrenalinecarboxylic acid. After a last injection of heparin, the treated mice were anesthetized with ethylether and the breast opened surgically. The blood was withdrawn from the heart and the lower portion of the heart ventricle was cut off. A catheter was inserted at the ventricle into the artery and fixed by means of binding threads. The two veins at the neck were opened surgically, and immediately physiological saline was injected through said catheter so that the remaining blood was entirely withdrawn at the opened veins together with the washing saline. The whole brain was removed from the sacrificed mouse, and the whole brain was dried in air at ambient temperature overnight. The dried brain was combusted in a sample-oxidizer (Packard TRY-CARBO 306) and the radioactivity of $^{14}$C-$CO_2$ obtained was determined by means of a liquid scintillation counter (Packard 4640) and the radioactivity as determined was calculated in term of the concentrations of L-threo-adrenalinecarboxylic acid. The test results obtained are summarized in Table 6 below.

TABLE 6

| Dosage of test compound | Concentrations (ng/brain) of ($^{14}$C)-L—threo-adrenalinecarboxylic acid under test in brain (mean value for five brains) Time after administration of test compound | | | |
|---|---|---|---|---|
| | 0.5 Hours | 1 Hour | 2 Hours | 8 Hours |
| 1 mg/kg | 16.2 | 19.9 | 15.3 | 5.88 |
| 10 mg/kg | 134 | 132 | 118 | 52.8 |
| 100 mg/kg | 1180 | 1224 | 832 | 396 |

It is observed that the concentration of ($^{14}$C)-L-threo-adrenalinecarboxylic acid in the brain as evaluated reached a maximum at a time of about 1 hour after the intravenous administration of the test compound, indicating a significant penetration of the test compound into brain through the blood-brain barrier, and also that the quantity of the test compound as transferred into and accumulated in the brain did not reach a saturation at dosages of the test compound of up to 100 mg/kg, suggesting that the quantity of the test compound as accumulated in the brain will increase with increased dosages of the test compound administered intravenously.

Test 7

The whole brains of mice of ddY-strain were homogenized and the resulting brain homogenate was diluted with the same volume of a buffere solution (comprising 50 mM Tris-HCl (pH 8.6, 1.5 mM EDTA.2Na); 0.5 mM Pridoxal-5-Phosphate; 1 mM Nialamide; and 0.85 mM L-ascorbic acid), and the mixture was centrifuged at 10,000 g to give a supernatant liquid containing the brain enzymes. To this supernatant liquid (500 $\mu$l) was added a solution containing 4.5 mM of a substrate selected from L-threo-adrenalinecarboxylic acid, L-threo-DOPS and L-DOPA. The mixture obtained (pH ca. 8, 1.0 ml) was incubated for 30 minutes at 37° C., followed by quantitative determination of adrenaline, noradrenaline or dopamine formed as the reaction product catecholamine.

The determination of the catecholamine as produced (adrenaline, noradrenaline or L-dopamine) was made according to the following procedure: Thus, the incubated mixture was admixed with aqueous 6% perchloric acid (PCA) for stopping the enzymatic reactions, and the reaction solution so obtained was de-salted by adding thereto potassium carbonate to precipitate the potassium perchlorate, and removing the precipitate by filtration. The de-salted reaction solution was passed through a column of Amberlite CG-50 as developed with 250 μl of 2N-PCA solution and then with 250μl of water. The eluate was analyzed by a high performance liquid chromatography under the following conditions:

Column: NUCLEOSIL $5C_{18}$ 4.6 mm I.D.×(50 mm+250 mm)

Mobile Phase: 0.1M Citrate buffer (pH 4.3)-methanol(9:1) containing 0.0025M 1-octane sulfonic acid sodium salt Flow rate: 700 μl/min.

Column temperature: 40° C.

Applied voltage: 600 mV vs. Ag/AgCl.

The yield of the catecholamine as formed was calculated in term of percentages based on the quantity of the substrate charged, and this calculated yield denotes the rate of decarboxylation of the substrate compound (in %). The tests was repeated 3 times or 5 times, and the average value of the test results are shown in Table 7 below.

TABLE 7

| Substrate | Substrate concentration (mM) | Yield of catecholamine as formed (%) |
| --- | --- | --- |
| L—threo-adrenaline-carboxylic acid | 4.5 | less than 0.00031 |
| L—threo-DOPS | 4.5 | more than 0.52 |
| L—DOPA | 4.5 | more than 11.7 |

EXAMPLE 1

A mixture of 100 mg of DL-threo-adrenalinecarboxylic acid, 40 mg of "Avicel" (cellulose for chromatographical use), 8 mg of carboxymethylcellulose, 3 mg of hydroxypropylcellulose and 2 mg of magnesium stearate was formed into tablets each in a size of 9 mm in diameter by 4 mm in thickness according to a conventional wet process for forming tablet.

EXAMPLE 2

A mixture of 200 mg of L-threo-adrenalinecarboxylic acid, 52 mg of lactose and 8 mg of magnesium stearate was formulated into capsules by packing into capsule case No. 3 by means of a conventional capsule-filling device.

What we claim is:

1. L-threo-3-(3,4-dihydroxyphenyl)-N-methylserine or a pharmaceutically acceptable salt or hydrate thereof.

2. A new substance essentially consisting of L-threo-3-(3,4-dihydroxyphenyl)-N-methylserine or a pharmaceutically acceptable salt thereof.

* * * * *